United States Patent [19]
Le Vay

[11] Patent Number: 5,166,528
[45] Date of Patent: Nov. 24, 1992

[54] MICROWAVE-ACTUATED ULTRAVIOLET STERILIZER

[76] Inventor: Thurston C. Le Vay, 635 Gloria Rd., Arcadia, Calif. 91006

[21] Appl. No.: 771,449

[22] Filed: Oct. 4, 1991

[51] Int. Cl.⁵ ............................................. A61L 2/12
[52] U.S. Cl. .......................... 250/455.11; 250/504 R; 422/24
[58] Field of Search ............. 250/455.1, 454.1, 504 R; 422/24

[56] References Cited

U.S. PATENT DOCUMENTS

| | | | |
|---|---|---|---|
| 2,407,379 | 9/1946 | Morehouse | 176/122 |
| 3,911,318 | 10/1975 | Spero et al. | 250/504 R |
| 3,926,556 | 12/1975 | Boucher | 21/54 R |
| 4,053,814 | 10/1977 | Regan et al. | 250/504 R |
| 4,354,668 | 11/1982 | Ury | 250/504 R |
| 4,448,750 | 5/1984 | Fuesting | 422/20 |
| 4,532,427 | 7/1985 | Matthews et al. | 250/504 R |
| 4,641,033 | 2/1987 | Petelin et al. | 250/504 R |
| 4,803,364 | 2/1989 | Ritter | 250/455.1 |
| 4,956,155 | 9/1990 | Rohrer et al. | 422/297 |
| 4,990,789 | 2/1991 | Uesaki | 250/504 R |

Primary Examiner—Jack I. Berman
Assistant Examiner—Kiet T. Nguyen
Attorney, Agent, or Firm—Christie, Parker & Hale

[57] ABSTRACT

A microwave activated ultraviolet sterilizer for surface sterilization of articles such as baby bottles, contact lenses and the like permits rapid irradiation and easy operation. The sterilizer includes a substantially non-conducting housing, a plurality of transparent ultraviolet lamps disposed within the housing, and a microwave source, such as a conventional home microwave oven. In use, the sterilizer is placed within the oven and derives its power from the oven's microwave field.

20 Claims, 3 Drawing Sheets

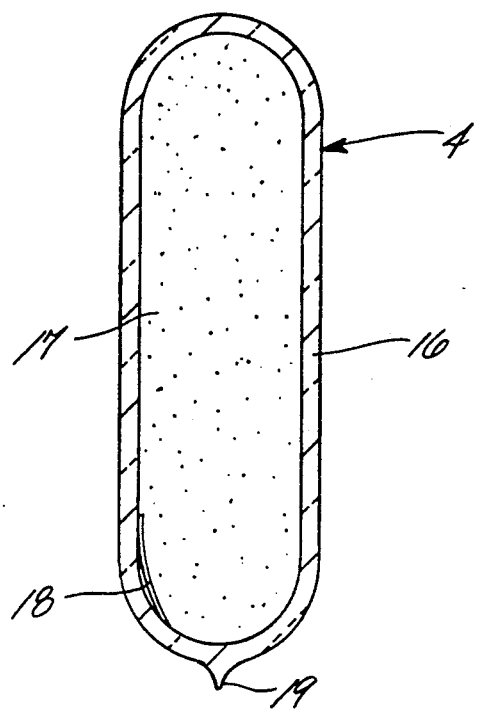
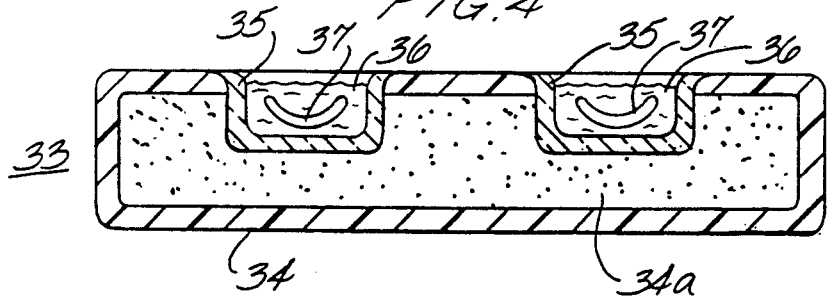
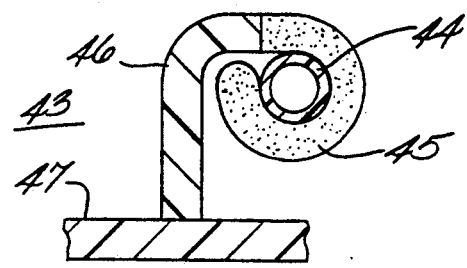

MICROWAVE-ACTUATED ULTRAVIOLET STERILIZER

FIELD OF INVENTION

The present invention relates to a microwave-actuated ultraviolet (UV) sterilizer for sterilizing or disinfecting articles. More particularly, the invention relates to such a sterilizer for home use which is suitable for readily sterilizing food items, baby bottles, contact lenses and the like.

BACKGROUND ART

Typically, people with weakened or impaired immune systems must disinfect or even sterilize their food and other items which will be ingested or which may otherwise transmit micro-organisms to their bodies. (In this application, "sterilization" includes "disinfection," i.e., "sterilization" means "sterilization or disinfection.") To surface sterilize articles such as baby bottles and contact lenses, the article usually is immersed in a solution or boiled. However, these methods are unsuitable for sterilization of an article which is heat labile or which must be frequently sterilized, since this immersion in liquids or boiling requires a relatively long time for effective sterilization. Therefore, a sterilization process which is quick and which does not involve substantial heating is desirable, so that it may be used with food such as fruit and vegetables.

The surface-sterilizing property of UV light has been described in the patent literature (see, for example, U.S. Pat. No. 2,407,379, issued Sep. 10, 1946). This patent describes a UV lamp for surface sterilization and general bactericidal use.

The concept of using UV light for surface sterilization is well known. For example, U.S. Pat. No. 4,803,364 (issued Feb. 7, 1989), describes a toothbrush conditioner which comprises a housing for a toothbrush and a UV light source inside. One places the toothbrush within a conditioning chamber and closes a lid containing the UV source. The UV source periodically emits radiation in sufficient quantities to effect surface sterilization.

U.S. Pat. No. 4,448,750 (issued May 15, 1984) describes a method for disinfecting and/or sterilizing small objects such as medical and dental instruments wherein the object to be disinfected or sterilized is contacted with a liquid such as an aqueous solution of sodium dodecylsulfate and carbamide. This solution is substantially transparent to UV radiation and has some bactericidal activity itself at normal temperatures, preferably about 25° C. While the articles are so submersed, vibrations in a frequency range of about 8–300 khz, preferably around 15 khz, are used to achieve a synergistic effect in destroying organisms. Additionally, simultaneous use of UV radiation in the wavelength range of about 1500Å to around 4,000Å preferably around 2537Å has a synergistic effect.

While the above-referenced methods of surface sterilization may find some applications, they are expensive, cumbersome, difficult to use at home, and have not enjoyed wide commercial success.

To overcome these and other problems, Boucher, in U.S. Pat. No. 3,926,556 (issued Dec. 16, 1975), describes a method and apparatus for low temperature intermittent or continuous destruction of microorganisms, including viruses, bacteria and fungi in both solid and liquid materials. The method is especially applicable for decontamination of organic fluids. The material to be sterilized is subjected to the synergistic effect of combined UV energy having a wavelength of around 40Å to around 3100Å and a microwave field having a wavelength from roughly 1 cm to about 35 cm while the temperature is maintained below about 100° C. Boucher's apparatus involves placing a UV-emitting lamp with a separate power source inside the chamber of a microwave oven. It is necessary that the oven have an electrical feedthrough to power the UV-emitting tube. Boucher's tube, of necessity, has electrodes attached thereto. Boucher notes that the bactericidal effect of the microwave energy is not due to thermal action but rather to the bipolar interaction of the oscillating microwave dipole with the molecules within the organisms themselves.

In view of the above, it would be desirable to provide a UV sterilizer such as described by Boucher which could be used in a conventional home microwave oven without the necessity of providing feedthroughs for electrical circuitry to power the UV source.

SUMMARY OF THE INVENTION

The present invention is a UV sterilizer formed by a gas contained in a bulb, which gas emits UV light in response to microwaves, and a microwave source.

In a preferred embodiment, the microwave source is a conventional microwave oven. Several bulbs are supported in a non-conductive, microwave-transparent housing, disposed in the microwave. In use, an object to be sterilized is placed in the housing, and the microwave oven is turned on, causing the gas to emit UV light at the object.

In other preferred embodiments, the sterilizer is adapted specifically for sterilizing contact lenses, bottles, baby bottle nipples and liquids. In the bottle sterilizer embodiment, a bulb mounts on a non-conductive base, and a bottle can be sterilized by placing it on the bulb so that the bulb is inside the bottle. In the contact lens sterilizing embodiment, a hollow non-conductive base supports two quartz wells formed in the base. The wells hold liquid and the lenses are disposed in respective wells. In the liquid sterilizing embodiment, the bulb is formed in the shape of a beaker to hold liquid. A non-conductive support is shaped to accommodate the bulb, or the beaker is made of a non-conductive material with a lid, and the bulb is attached to the lid and immersed in the liquid when the lid is on the beaker. In the nipple sterilizing embodiment, the nipple is friction fit into a hook-shaped bulb.

BRIEF DESCRIPTION OF THE DRAWINGS

FIG. 2 is a longitudinal sectional view of a UV bulb according to the present invention.

FIG. 4 is a sectional view of a UV sterilizer of a third embodiment adapted for contact lenses.

FIG. 5 is a sectional view of a UV sterilizer of a fourth embodiment adapted for nipples of baby bottles.

DETAILED DESCRIPTION OF THE PREFERRED EMBODIMENTS

In general, the invention is a UV sterilizer adapted for home use. The sterilizer includes a quartz bulb containing mercury vapor or any other appropriate gas at low pressure which emits UV light when placed in a microwave field. The microwave field stimulates intense emission of UV light from the vapor within the bulb. The light in combination with the microwave field is bactericidal and can be used for the cold sterilization of objects placed near the bulb. It has been found that the UV light so generated in combination with the microwave intensities normally available within a consumer microwave oven are sufficient to destroy most organisms at the surface of items such as combs, fruit, toothbrushes and even water and other fluids.

Figure 1:
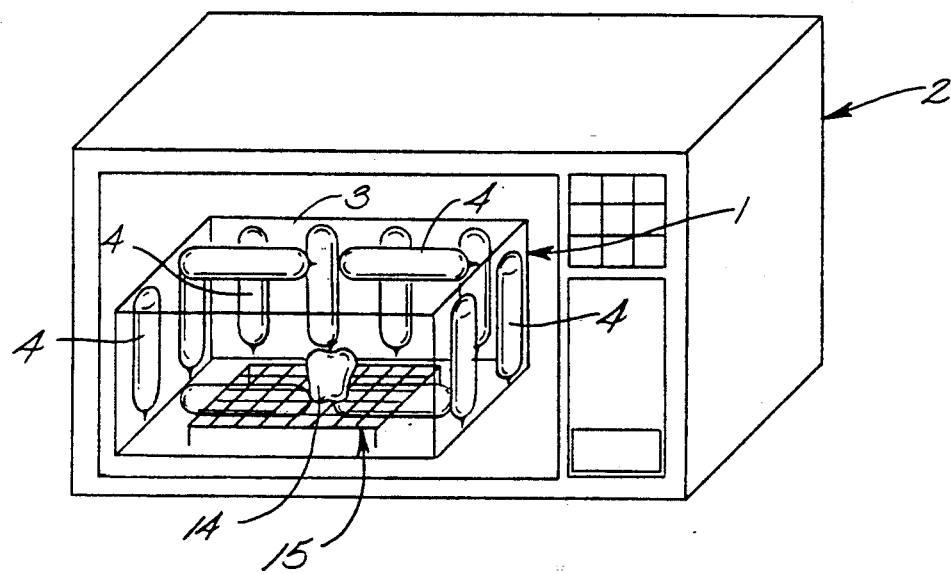
FIG. 1 is a perspective view of the UV sterilizer of one embodiment of the present invention housed within a conventional microwave oven.

Turning now to FIG. 1, a sterilizing unit 1 is placed within a chamber of a conventional microwave oven 2. Unit 1 is adapted to emit UV light in response to microwaves, and thus obviates the need for a separate power supply. Unit 1 consists of a non-conductive, microwave transparent housing 3 of ceramic or plastic (preferably thermoplastic) which is box-like, and a UV source of one or more UV bulbs 4 mounted (e.g., by a microwave-resistant and UV-resistant adhesive or by plastic brackets or slots) to the inside of the walls, ceiling and floor of housing 3. The housing may have an open or a partially open side (also supporting bulbs as appropriate) through which to insert objects. The bulbs 4 are made of a UV transparent material, preferably quartz, and filled with a UV-emitting gas, preferably mercury, at low pressure. The gas is selected so that it will emit UV light in response to microwaves.

An object 14 or article to be sterilized, such as an apple, is placed within housing 3 close to the bulbs 4. The sterilizer is preferably constructed to avoid "shadowing," regardless of the orientation in which the user places the object in the housing. Accordingly, all surfaces of the article will be simultaneously exposed to UV light so that the article is fully sterilized in one step. To help avoid shadowing, a stand 15 with a UV transmitting surface may be provided to support the object. The housing is also preferably constructed of a size and shape which will accommodate as many different sizes and shapes of articles as possible, yet have the articles as close to the UV light as possible to minimize transmission loss.

To sterilize, the microwave is turned on. Surface sterilization is achieved in a relatively short time, e.g., 30 to 40 seconds, and thus any heating due to the microwaves is limited. The sterilization time depends on a number of factors, such as how close the UV lamps are to the object, how strong the UV rays are, and the microorganisms to be killed. For example, FDA standards require sterilization sufficient to kill aspergillis niger, which can be achieved in as low as 20 seconds or less of UV exposure in the inventive sterilizer. Therefore, 30 or 40 seconds provides some margin of safety. Greater exposure times provide greater safety, but take longer and thus tend to subject the object to heating.

It should be noted that sterilizer 1 preferably has the bulbs 4 mounted on the inside of housing 3 to be closest to the object, but the bulbs can be mounted to the outside as long as the housing is UV transmitting. The housing can also be formed as a frame, with the bulbs extending between bars of the frame. Moreover, the housing and bulbs may even be formed as one element, by providing the housing of a UV transmitting material which itself encases the UV-emitting gas.

A sectional view of a bulb 4 is shown in FIG. 2. Each bulb is a UV transparent envelope 16 housing a UV-emitting gas 17. The envelope is preferably quartz, which has a relatively high UV transparency. Other UV transparent materials may be used, but the exposure time must be increased for lesser transparency. However, quartz is relatively expensive, and therefore the sterilizer is preferably constructed to minimize its use.

To construct the bulb, mercury, preferably along with a carrier gas such as argon or neon, is introduced at low pressures (e.g., about 1 mm of mercury) into an evacuated tube. Then, the tube is sealed, typically forming a nipple 19. The carrier gas functions to minimize the amount of mercury needed in the tube. In addition, the gas can function to help determine whether or not UV emission has started. For example, neon will emit a red color in response to microwaves while mercury will emit a bluish white color. If the bulb appears red, UV emission has not started. The exposure time is thus determined based on the time the bulb appears bluish white.

To enhance UV light emission, it is particularly useful to place a conductor or semi-conductor such as a piece of nichrome or tungsten wire 18 inside the tube before sealing. The wire should be small, e.g., in the range of 0.001 to 0.005 inch diameter and about 1-2 inches long, to avoid appreciable heat production in response to the microwaves. The wire acts like an antenna and facilitates the breakdown or ionization of the gas within the tube and the emission of UV light. It should be noted that mercury may be in its liquid state prior to stimulation by the microwaves, but will become gaseous upon stimulation.

Figure 3:
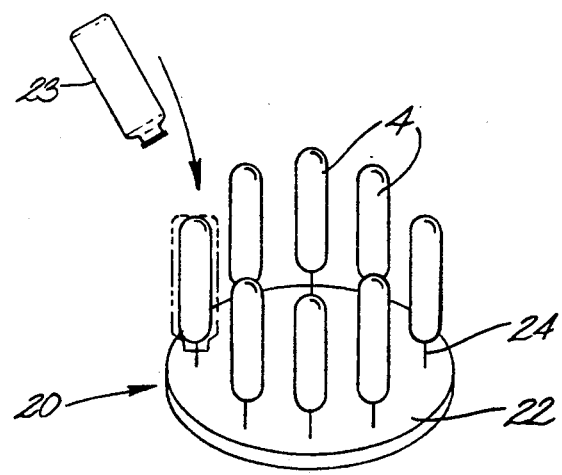
FIG. 3 shows a UV sterilizer of a second embodiment adapted for bottles.

FIG. 3 shows sterilizer 20 adapted for bottles, especially baby bottles. Sterilizer 20 shows an array of UV-emitting bulbs 4 supported on a non-conducting base 22 by means of non-conducting supports 24. The bulbs 4 are dimensioned (e.g., 6" to 7" long) to fit within the interior of a variety of microwave transparent bottles 23. In use, the bottles are placed over the bulbs 4 and the sterilizer 20 is placed within the chamber of a conventional microwave oven. Such a sterilizer can be used in the home, or even in institutions such as hospital maternity wards and day care centers.

FIG. 4 is a sectional view of a sterilizer 33 adapted for hard contact lenses. The sterilizer is formed by a non-conducting base 34 having a hollow section 34a and formed with two openings in which thimble-shaped wells 35 are disposed. The wells are labeled for right and left lenses and are made of UV transmitting material such as quartz. They are shaped to hold liquid 36 in which lenses 37 are placed. The bulb is thus formed by the entire sterilizer, as hollow section 34a contains the UV-emitting gas. To use the sterilizer, liquid 36 and a lens 37 are placed in each well 35, and the sterilizer is placed in a microwave oven. When the microwave is on, the gas irradiates the lenses through the quartz wells.

In this embodiment, the wells may be attached to the base by adhesive or other means suitable for joining quartz and ceramic in an airtight fashion. For example, silicone or epoxy cement could be used to join the quartz and ceramic. The use of ceramic as a base with quartz wells minimizes the use of quartz, which is relatively expensive. More specifically, by constructing the base entirely of ceramic with only the portion where UV light must be transmitted, i.e., the wells formed of quartz, the amount of quartz is greatly reduced. However, the entire sterilizer could be made of quartz. To protect the quartz in this embodiment and others from breaking and/or shattering upon breakage, a UV transparent teflon coating may be applied to the quartz.

In FIG. 5, which is a sectional view of a sterilizer 43 adapted for sterilizing the outside of a baby bottle nipple 44, the nipple is friction fit inside a hook-shaped bulb 45 containing a UV-emitting gas. The bulb is attached to a non-conductive arm 46 in turn mounted on or integral with a platform 47.

Figure 6:
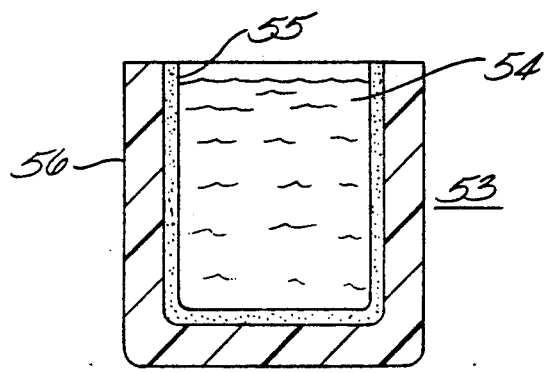
FIG. 6 is a sectional view of a UV sterilizer of a fifth embodiment adapted for liquids.

In FIG. 6, which is a sectional view of a sterilizer 53 adapted for sterilizing a liquid 54, such as water or juice, a bulb 55 containing UV-emitting gas is shaped like a beaker to hold the liquid. The bulb may form the entire sterilizer. However, to limit the use of UV transmitting material while providing additional strength and stability, the bulb is shown mounted to the inside of a beaker-shaped non-conducting material 56.

Figure 7:
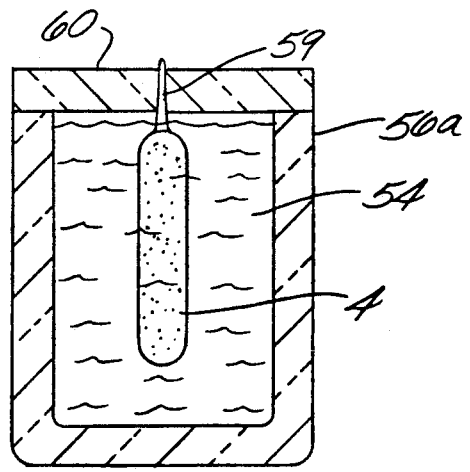
FIG. 7 is a sectional view of a UV sterilizer illustrating a modification of the fifth embodiment.

Alternatively, to sterilize a liquid, a bulb such as bulb 4 of FIG. 2, may be inserted into liquid 54 to sterilize it. This is shown in the sectional view of FIG. 7. A beaker 56a of a nonconductive, microwave transparent material holds liquid 54. A bulb 4, having a stem 59 fixed to it and held in a non-conductive microwave transparent lid 60, is immersed in the liquid.

The invention thus achieves an inexpensive sterilizer that can be readily used in the home in an existing microwave oven, which already provides appropriate safeguards against user exposure to harmful radiation. For example, the microwave walls and window block UV light or can readily be made to do so In addition, the microwaves, and thus the UV emissions, shut off in response to premature opening of the oven door.

It is to be understood that numerous modifications may be made in the illustrative embodiment of the invention and other arrangements may be devised without departing from the spirit and scope of the invention as set forth in the appended claims. For example, the invention may be useful for production of UV light for processes such as erasing EPROMS and curing resins, in addition to sterilization.

I claim:

1. A method of sterilizing an object using ultraviolet light emitted from a gas capable of emission of ultraviolet light in response to microwaves, comprising the steps of:
   placing an object to be sterilized in position to receive ultraviolet light emitted from at least one bulb containing the gas, and
   irradiating the bulb with microwaves to stimulate the gas to emit ultraviolet light at the object,
   wherein the at least one bulb and the object are placed in a microwave oven, and the step of irradiating comprises turning on the oven.

2. The method of claim 1, wherein the step of irradiating further comprises irradiating the bulb for a sufficient time for the ultraviolet light to sterilize the surface of the object.

3. The method of claim 1, further comprising a step of positioning the object to be sterilized with the at least one bulb surrounding it.

4. The method of claim 1, wherein the at least one bulb is adapted to fit inside the object, and, in the step of placing, the object is placed around the bulb.

5. The method of claim 1, further comprising a step of turning off the microwave oven in response to opening a door of the oven.

6. The method of claim 1, wherein the step of placing the at least one bulb in the microwave oven comprises placing the bulb in the oven for free movement with respect to the oven, whereby the bulb is freely insertable and removable from the oven.

7. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises a microwave-transparent housing and a plurality of bulbs, containing the gas, mounted inside the housing for irradiating ultraviolet light at an object disposed in the housing.

8. A device according to claim 7, further comprising a non-conductive microwave transparent stand for supporting the object in the housing.

9. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises an elongate bulb containing the gas and a non-conductive base for mounting the bulb, whereby a microwave transparent bottle may be supported with the bulb inside for sterilizing the inside of the bottle.

10. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises a quartz bulb containing the gas, and the bulb has a beaker-like shape for containing liquids, whereby the liquids may be placed in the bulb for sterilization.

11. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises at least one quartz bulb containing the gas, and wherein the at least one bulb comprises a hollow non-conductive base having two wells formed of a UV-transmitting material, and the gas is disposed in the hollow base, whereby liquid may be placed in each well along with an object to be sterilized.

12. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises at least one bulb containing the gas and a relatively small amount of a conductive material.

13. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises a non-conductive base, and a bulb containing the gas, and wherein the bulb has a hook-like shape, whereby a baby bottle nipple may be frictionally supported in the hook for sterilization of the nipple.

14. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises at least one quartz bulb containing the gas, and wherein there is one bulb which is adapted to be supported inside a non-conductive base having a beaker-like shape for containing liquids.

15. A device for sterilization of articles comprising a sterilizer unit containing a gas capable of emitting ultraviolet light in response to microwaves, and a microwave source for irradiating the gas to cause the gas to emit ultraviolet light, wherein the sterilizer unit comprises a container for holding a liquid, a lid for the containing, and a bulb containing the gas and fixed to the lid, whereby the bulb is immersible in the liquid by positioning the lid on the container.

16. A device for sterilization of articles comprising a sterilizer unit containing a gas capable of emitting ultraviolet light in response to microwaves, and a microwave source for irradiating the gas to cause the gas to emit ultraviolet light, wherein the microwave source is a microwave oven and the sterilizer unit is disposed in the oven.

17. A device according to claim 16, wherein the sterilizer unit is unconnected to the microwave oven, whereby the sterilizer unit is freely insertable and removable from the microwave oven.

18. A device according to claim 16, wherein the microwave oven has a door, and the microwaves turn off in response to opening the door.

19. A device according to claim 16, wherein the at least one bulb is adapted to surround the object.

20. A device according to claim 16, wherein the at least one bulb is adapted to fit inside the object.

* * * * *

UNITED STATES PATENT AND TRADEMARK OFFICE
CERTIFICATE OF CORRECTION

PATENT NO. : 5,166,528
DATED      : November 24, 1992
INVENTOR(S) : Thurston C. Le Vay It is certified that error appears in the above-identified patent and that said Letters Patent is hereby corrected as shown below:

On the title page

[56] References Cited, U.S. PATENT DOCUMENTS, change
      "4,354,668  11/1982  Ury...250/504R" to
   -- 4,359,668  11/1982  Ury...250/504R --.

Column 5, line 34, after "so" insert a period.

Column 7, lines 11,12, change "containing" to -- container --.

Signed and Sealed this

Twenty-third Day of November, 1993

Attest:

BRUCE LEHMAN

Attesting Officer

Commissioner of Patents and Trademarks